United States Patent
Le-Thiesse

(10) Patent No.: US 9,388,108 B2
(45) Date of Patent: Jul. 12, 2016

(54) COMPOUNDS INCLUDING VANILLIN AND ETHYLVANILLIN AND METHODS OF MAKING AND USING THE SAME

(75) Inventor: Jean-Claude Le-Thiesse, Saint-Etienne (FR)

(73) Assignee: Rhodia Operations, Paris (FR)

( * ) Notice: Subject to any disclaimer, the term of this patent is extended or adjusted under 35 U.S.C. 154(b) by 340 days.

(21) Appl. No.: 13/125,833

(22) PCT Filed: Oct. 8, 2009

(86) PCT No.: PCT/EP2009/063093
§ 371 (c)(1),
(2), (4) Date: Jun. 6, 2011

(87) PCT Pub. No.: WO2010/046239
PCT Pub. Date: Apr. 29, 2010

(65) Prior Publication Data
US 2011/0230565 A1  Sep. 22, 2011

(30) Foreign Application Priority Data
Oct. 24, 2008 (FR) ...................................... 08 05913

(51) Int. Cl.
| | | |
|---|---|---|
| *A01N 35/00* | (2006.01) | |
| *A61K 31/11* | (2006.01) | |
| *A23L 1/22* | (2006.01) | |
| *A23L 2/56* | (2006.01) | |
| *C07C 47/58* | (2006.01) | |
| *A23L 1/221* | (2006.01) | |
| *A61K 8/34* | (2006.01) | |
| *A61Q 13/00* | (2006.01) | |
| *C07C 45/81* | (2006.01) | |
| *C07C 47/575* | (2006.01) | |

(52) U.S. Cl.
CPC ................. *C07C 47/58* (2013.01); *A23L 1/221* (2013.01); *A61K 8/347* (2013.01); *A61Q 13/00* (2013.01); *C07C 45/81* (2013.01); *C07C 47/575* (2013.01); *A61K 2800/592* (2013.01)

(58) Field of Classification Search
USPC .......................................... 514/699; 426/538
See application file for complete search history.

(56) References Cited

U.S. PATENT DOCUMENTS

| | | | | |
|---|---|---|---|---|
| 5,807,584 | A | * | 9/1998 | Thiesse et al. ................ 424/489 |
| 2012/0103786 | A1 | | 5/2012 | Gayet et al. |
| 2012/0277321 | A1 | | 11/2012 | Le-Thiesse et al. |

FOREIGN PATENT DOCUMENTS

PL          54711      2/1968

OTHER PUBLICATIONS

Zenon et. al. (Food essence with vanilla flavor, Chemical Abstracts (1969).*
International Search Report dated Jan. 12, 2010 issued in PCT/EP2009/063093.
Zenon et al., "Food Essence With Vanilla Flavor" (Chemical Abstract).
Szczepanik, R. et al.—"Effect of intermolecular interactions between vanillin and ethylvanillin on the technology and aroma of food flavoring additives"; (1969) Roczniki Technologii i Chemii Zywnosci, vol. 15, pp. 87-99 (15 pages)—including Abstract in English.
Devoe, H., Editor—"Phase Diagrams: Binary Systems" in Chapter 13 (Section 13.2)—The Phase Rule and Phase Diagrams, Thermodynamics and Chemistry (2012) $2^{nd}$ edition, Version 4, published by Howard DeVoe, pp. 426-431 (8 pages).
Atkins, P. et al., Editors—"Liquid-solid phase diagrams" in Chapter 6 (Section 6.6)—Phase Diagrams in textbook entitled "Atkins' Physical Chemistry" (2006) $8^{th}$ edition, published by W.H. Freeman and Company, New York, pp. 189-191 (6 pages).
Slaughter, D. W. et al.—"Calculation of Solid-Liquid Equilibrium and Crystallization Paths for Melt Crystallization Processes", Chemical Engineering Science (1995) vol. 50, No. 11, pp. 1679-1694, Elsevier Science Ltd (16 pages).
Ronkart, S. N. et al.—"Phénomène de la transition vitreuse appliquée aux glucides alimentaires amorphes à l'état de poudre", Biotechnol. Agron. Soc. Environ., (2009) vol. 13, No. 1. pp. 177-186 (10 pages)—accesibe online at http://popups.ulg.ac.be/Base/document.php?id=3686, English translation included.

* cited by examiner

*Primary Examiner* — Marcos Sznaidman
(74) *Attorney, Agent, or Firm* — Osha Liang LLP

(57) ABSTRACT

A compound that includes vanillin and ethylvanillin, and a method for making same are described. The compound described can be obtained by the co-crystallization of vanillin and ethylvanillin. Methods of using the compound in numerous applicable fields, particularly in human and animal food are also described.

41 Claims, 4 Drawing Sheets

COMPOUNDS INCLUDING VANILLIN AND ETHYLVANILLIN AND METHODS OF MAKING AND USING THE SAME

This application is the United States national phase of PCT/EP2009/063093, filed Oct. 8, 2009, and designating the United States (published in the French language on Apr. 29, 2010, as WO 2010/046239 A1; the title and abstract were also published in English), which claims priority under 35 U.S.C. §119 of FR 0805913, filed Oct. 24, 2008, each hereby expressly incorporated by reference in its entirety and each assigned to the assignee hereof.

The present invention relates to a novel compound based on vanillin and ethylvanillin and the method of preparation thereof.

More precisely, the invention relates to a novel compound obtained by co-crystallization of vanillin and ethylvanillin.

The invention also relates to the use thereof in many fields of application, notably in human and animal nutrition.

Vanillin, or 4-hydroxy-3-methoxybenzaldehyde, is a product that is widely used in a great many fields of application as a flavoring agent and/or perfume.

Thus, vanillin is consumed abundantly in the food and animal-feed industry but it also has applications in other areas, for example pharmacy or perfumery. Consequently, it is a product with a high level of consumption.

Vanillin is very often combined with ethylvanillin or 3-ethoxy-4-hydroxybenzaldehyde, as it is known that the presence of a small amount of ethylvanillin can intensify the perfuming and/or organoleptic properties of vanillin.

Thus, a potential user would like to be provided with a ready-made mixture of vanillin and ethylvanillin.

The problem that arises is that preparing said mixture by a conventional technique of dry mixing of powders of vanillin and ethylvanillin results in a mixture that is very liable to form lumps. As a result, it is impossible to use such a mixture on account of its presentation, which is not in pulverulent form, and there is considerable difficulty in dissolving the mass obtained.

Moreover, prolonged storage leads to a worsening of the phenomenon of lumpiness, leading to caking of the powder.

Thus, the aim of the invention is to provide a novel presentation based on vanillin and ethylvanillin that has improved flowability and absence of lumpiness on storage.

Now, a novel compound has been found, which forms the object of the present invention, obtained by co-crystallization of vanillin and ethylvanillin used in a vanillin/ethylvanillin molar ratio of 2.

Another object of the invention is the method of obtaining said compound from vanillin and ethylvanillin, characterized in that it comprises the co-crystallization of vanillin and ethylvanillin used in a vanillin/ethylvanillin molar ratio of 2, in a molten medium or in solution in a solvent that dissolves them.

According to the invention, it was found that the compound obtained by co-crystallization of vanillin and ethylvanillin in a molar ratio of 2 (corresponding to a 65/35 weight ratio) exhibited unique characteristics.

It is in the form of a white powder, which has a melting point, measured by differential scanning calorimetry, of 60° C.±2° C., different from that of vanillin and ethylvanillin, of 81° C.±1° C. and 76° C.±1° C., respectively.

The compound of the invention possesses its own specific X-ray diffraction spectrum, which is different from that of vanillin and ethylvanillin.

FIG. 1 shows three curves corresponding to the different X-ray diffraction spectra of the compound of the invention, of vanillin and of ethylvanillin.

On the spectrum of the compound of the invention based on vanillin and ethylvanillin, we note in particular the presence of lines at angles $2\theta$ (in °)=20.7-25.6-27.5-28.0; said lines being absent from the X-ray diffraction spectra of vanillin and ethylvanillin.

Another characteristic of the compound of the invention is that its X-ray diffraction spectrum does not change significantly during prolonged storage.

The variation of its spectrum was traced as a function of the storage time at room temperature. Over a period of prolonged storage (5 months), absolutely no change is observed in the spectrum of the compound of the invention, as evidenced by FIG. 2, which is explained in example 1.

It is found that there is no change in the specific lines of the compound of the invention.

Another characteristic of the compound of the invention is that it is a compound with no or very little hygroscopicity, like vanillin and ethylvanillin.

The hygroscopicity of the compound of the invention is determined by measuring its weight change after being held for 1 hour at 40° C. in air at 80% relative humidity.

Said compound adsorbs less than 0.5 wt. % of water, and its content is preferably between 0.1 and 0.3 wt. %; of water. Said compound remains perfectly solid.

It should be noted that patent PL 54 771 describes a food flavoring agent comprising 57 wt. % of vanillin and 43 wt. % of ethylvanillin. This mixture has a composition different from the product of the invention and has physicochemical characteristics different from the product of the invention.

According to PL 54 77, this so-called eutectic mixture has a melting point of 49° C., compared with 60° C. for the product of the invention.

Another major difference is with respect to its properties of hygroscopicity. In fact, a mixture comprising 57 wt. % of vanillin and 43 wt. % of ethylvanillin heated to 40° C. in air at 80% relative humidity adsorbs more than 3 wt. % of water and becomes pasty or even partially liquid in these conditions. It is therefore impossible to store or use this mixture under climatic conditions of high temperature and/or humidity frequently encountered in certain geographical zones, whereas the product of the invention remains perfectly solid and can be handled easily.

Thus, the compound of the invention has greatly improved properties of lumpiness relative to simple dry mixing of vanillin and ethylvanillin.

Said dry mixture with a weight ratio VA/EVA between 2/98 and 98/2 shows a weight increase after storage at room temperature (22° C.) in less than a week, whereas the compound of the invention stored in the same conditions shows no weight increase after a month, or even after several months (for example at least 6 months).

The compound of the invention has good organoleptic properties.

It possesses high flavoring power, far greater than that of vanillin. Thus, in its applications as flavoring agent, smaller amounts, for example amounts that have been halved, can be used without finding any difference in flavoring power.

The particular properties of the compound of the invention are connected by two parameters, namely the molar ratio of vanillin to ethylvanillin, and the fact that there is co-crystallization between vanillin and ethylvanillin in a specific crystalline form, characterized by its melting point and its X-ray diffraction spectrum.

Another object of the invention is therefore the method of obtaining the compound of the invention.

According to the invention, it was found that the novel compound of vanillin and ethylvanillin displays improved properties of lumpiness when it is obtained by co-crystallization of vanillin and ethylvanillin used in a molar ratio of 2.

A first embodiment of the method of preparation consists of carrying out the co-crystallization of vanillin and ethylvanillin in a solvent.

Another embodiment consists of carrying out co-crystallization by an operation of melting followed by solidification by cooling at controlled temperature.

The method of the invention uses vanillin and ethylvanillin in a vanillin/ethylvanillin molar ratio of 2, corresponding to a mixture by weight comprising 65% of vanillin and 35% of ethylvanillin.

According to one embodiment of the invention, the vanillin and ethylvanillin are dissolved in a solvent.

The solvent that is to be used must be chemically inert with respect to vanillin and ethylvanillin and must remain inert during heating in the temperature range defined hereunder.

As solvents to be used in the compositions of the invention, it is preferable to use a protic or aprotic polar solvent, or a mixture of solvents.

Examples of solvents that are entirely suitable for the present invention are given below:
water,
alcohols, preferably aliphatic or arylaliphatic and more preferably methanol, ethanol, propanol, isopropanol, butanol, β-phenylethyl alcohol, ethylene glycol, diethylene glycol, propylene glycol, glycerol,
ethers, preferably aliphatic, and more particularly diethyl ether, dipropyl ether, diisopropyl ether, dibutyl ether, methyl tert-butyl ether, ethyl tert-butyl ether, ditert-butyl ether, diisopropyl ether, dibutyl ether, methyl tert-butyl ether, ethyl tert-butyl ether, ditert-butyl ether, ethylene glycol dimethyl ether, diethylene glycol dimethyl ether,
alkyl or aralkyl esters of aliphatic, cycloaliphatic or aromatic carboxylic acids, and more preferably ethyl acetate, butyl acetate, benzyl salicylate, methyl laurate, methyl benzoate, ethyl citrate, triacetylglycerol or triacetin, glycerol ester and acetic acid.

The above list is not exhaustive.

Water, ethanol, propylene glycol, triacetin and mixtures thereof are preferably selected from the aforementioned solvents.

Regarding the amount of solvent used, its amount depends on the nature of the solvent and on the dissolution temperature. The amount is greater for lower dissolution temperatures.

The amount of solvent used, expressed by weight relative to the weight of dry matter (vanillin+ethylvanillin) generally varies between 5 and 60%.

Depending on the amount of solvent used relative to the weight of dry matter, the mixture can optionally be heated to a temperature preferably between 40° C. and 90° C. and more preferably between 50° C. and 80° C. to facilitate dissolution of the vanillin and ethylvanillin.

According to another embodiment, the solvent is heated to the temperature defined above and then the vanillin and ethylvanillin are introduced in a molar ratio of 2.

Stirring of the mixture continues until a homogeneous solution is obtained. Generally this takes between 10 and 120 min.

Then the solution thus obtained is cooled to bring about crystallization of the compound of the invention.

If the solution was prepared between 40° C. and 90° C., cooling to room temperature is generally sufficient, but it can also be carried out as far as a temperature of 0° C.

"Room temperature" means a temperature between 15° C. and 25° C., preferably between 18° C. and 22° C.

If the solution was prepared at room temperature, cooling to a temperature between 0° C. and 10° C. and more preferably between 0° C. and 5° C. is necessary to bring about crystallization of the compound of the invention.

Whatever variant of preparation is used, the crystallized product is separated by the conventional techniques of solid/liquid separation, preferably by filtration or centrifugation.

Then an operation of drying is carried out; this can be carried out in a conventional device for drying, for example a furnace, a plate-type dryer, a fluidized bed, a vacuum stove, etc.

Drying can be carried out in air or in an inert gas atmosphere, preferably in a nitrogen atmosphere. Drying can also be carried out in a chamber under reduced pressure, for example at a pressure between 10 and 500 mm of mercury.

Drying is carried out by heating the crystals of the compound obtained to a temperature of 51° C.±1° C.

The drying time is generally from 15 min to 2 hours.

A compound is obtained having the properties defined above.

A variant of the method of the invention consists of preparing the compound of the invention according to an operation that consists of melting the mixture of vanillin and ethylvanillin used in a molar ratio of 2 and then cooling the molten mixture by lowering the temperature to 50° C.±1° C., then this temperature is maintained until the mixture has solidified completely.

According to a preferred variant of the method of the invention, cooling is effected in the absence of any stirring.

For this purpose, vanillin and ethylvanillin, used in a molar ratio of 2, are charged separately or mixed together and the mixture is heated to a temperature that is selected between 60° C. and 90° C. and that is preferably between 70° C. and 80° C.

This operation is generally carried out with stirring in any device, and notably in a tank equipped with a conventional heating device, for example a system for heating by electrical resistance or else by circulation of a heat-transfer fluid in a double jacket or in a heated chamber such as a furnace or stove.

It is desirable to carry out the preparation of this molten mixture under an atmosphere of inert gas, which is preferably nitrogen.

The mixture is maintained at the selected temperature until the molten mixture is obtained.

The molten product is transferred to any container, for example a stainless steel tray, that will permit easy recovery of the product after solidification. This container is preheated between 70 and 80° C. before it receives the molten mixture.

In a subsequent stage, the molten mixture is cooled to a temperature of 50° C.±1, by controlling the temperature of cooling by any known means.

As mentioned previously, cooling is preferably carried out in the absence of any stirring.

The solidified mixture obtained can be formed, for which various techniques can be envisaged.

One technique consists of grinding the mixture obtained in such a way that the particle size is compatible with the application envisaged.

Most often this is from 100 μm to 2 mm.

Generally, the particle size expressed by the median diameter ($d_{50}$) varies from 100 μm to 800 μm, preferably between 200 μm and 300 μm. The median diameter is defined as being such that 50 wt. % of the particles have a diameter greater than or less than the median diameter.

The operation of grinding can be carried out in conventional equipment such as a blade mill, a toothed roll crusher, or a granulator.

Another shaping can be carried out using the technique of flake formation on a drum or belt.

A molten mixture of vanillin and ethylvanillin is prepared in the proportions stated previously. The molten mixture is then brought in contact with a metal drum or belt cooled to a temperature of 50° C., then the film obtained on the drum is scraped with a blade, to recover the solid mixture of vanillin and ethylvanillin in the form of flakes.

Owing to this stage of co-crystallization, the method of the invention makes it possible to obtain a novel compound of vanillin and ethylvanillin that has improved storage properties, as the phenomenon of lump formation is greatly reduced, as is demonstrated in the examples.

The invention does not exclude the use of one or more excipients with the compound of the invention.

It should be noted that the choice of excipient or excipients must take into account the intended use of the final product and therefore it must be edible if it is used in the food sector.

The amount of excipient(s) can be very variable and it can represent from 0.1 to 90% of the weight of the final mixture.

It is selected advantageously between 20 and 60 wt. %.

Depending on the type of excipient adopted, the amount used and the intended use of the final product, the excipient can either be added by dry mixing with the compound of the invention, or incorporated in the method of production of the compound of the invention, for example during the stage of melting of the mixture of vanillin and ethylvanillin.

Examples of excipients that can be used are given below, but are not in any way limiting.

Fats represent a first type of excipient.

As examples, we may mention fatty acids, optionally in the form of salts or esters.

The fatty acids used are generally long-chain saturated fatty acids, i.e. having a chain length between about 9 and 21 carbon atoms, for example capric acid, lauric acid, tridecyl acid, myristic acid, palmitic acid, stearic acid, behenic acid.

It is possible that said acids are in salified form and we may notably mention calcium or magnesium stearate.

As esters of fatty acids, we may mention in particular glyceryl stearate, isopropyl palmitate, cetyl palmitate, isopropyl myristate.

We may also mention more specifically the esters of glycerol and of long-chain fatty acids such as glycerol monostearate, glycerol monopalmitostearate, glycerol palmitostearate, ethylene glycol palmitostearate, polyglycerol palmitostearate, polyglycol 1500 and 6000 palmitostearate, glycerol monolinoleate; optionally mono- or diacetylated glycerol esters of long-chain fatty acids such as monoacetylated or diacetylated monoglycerides and mixtures thereof; semisynthetic glycerides.

We may also add a fatty alcohol whose chain of carbon atoms is between about 16 and 22 carbon atoms, for example myristyl alcohol, palmityl alcohol, stearyl alcohol.

It is also possible to use polyethoxylated fatty alcohols resulting from condensation with ethylene oxide at a rate of 6 to 20 moles of ethylene oxide per mole, of linear or branched fatty alcohols having from 10 to 20 carbon atoms, for example copra alcohol, tridecanol or myristyl alcohol.

We may also mention waxes such as microcrystalline waxes, white wax, carnauba wax, paraffin.

We may mention sugars, for example glucose, sucrose, fructose, galactose, ribose, maltose, sorbitol, mannitol, xylitol, lactitol, maltitol; invert sugars: glucose syrups as well as sucroglycerides derived from fatty oils such as copra oil, palm oil, hydrogenated palm oil and hydrogenated soya oil; sucroesters of fatty acids such as sucrose monopalmitate, sucrose monodistearate and sucrose distearate.

As examples of other excipients, we may mention the polysaccharides, and we may mention, among others, the following products and mixtures thereof:

starches derived notably from wheat, maize, barley, rice, manioc or potato, native, pregelatinized or modified and more particularly the amylose-rich native maize starches, pregelatinized maize starches, modified maize starches, modified waxy maize starches, pregelatinized waxy maize starches, modified waxy maize starches in particular the OSSA/sodium octenylsuccinate starch, starch hydrolyzates, dextrins and maltodextrins resulting from the hydrolysis of a starch (wheat, maize) or of a potato flour, as well as β-cyclodextrins, cellulose, its ethers, notably methylcellulose, ethylcellulose, methylethylcellulose, hydroxypropylcellulose; or its esters, notably carboxymethylcellulose or carboxyethylcellulose optionally in the sodium-containing form, gums such as gum of kappa carrageenan or iota carrageenan, pectin, guar gum, carob gum, and xanthan gum, alginates, gum arabic, acacia gum, agar-agar.

Preferably a maltodextrin is selected having a degree of hydrolysis measured by "dextrose equivalent" or DE below 20 and preferably between 5 and 19 and more preferably between 6 and 15.

As other excipients, we may mention flours, notably wheat flour (native or pregel); starches, more particularly potato starch, Toloman starch, maize starch, cornflour, sago or tapioca.

As excipients, it is also possible to use gelatin (preferably having a gelling strength measured using a gelometer of 100, 175 and 250 Bloom). It can either be from acid treatment of pigskins and osseine, or from alkaline treatment of cowhides and osseine.

It is also possible to add other excipients such as silica or for example an antioxidant such as notably vitamin E or an emulsifier, notably lecithin.

In order to adjust the flavoring power of the mixture or enhance its taste, the use of ethylmaltol and/or of propenylguetol can be envisaged.

The invention does not exclude the addition of a supplementary amount of vanillin or ethylvanillin.

The preferred compositions of the invention comprise a sugar, preferably glucose, sucrose, fructose and/or a dextrin or maltodextrin: the latter having a DE advantageously between 6 and 15.

The excipients are selected as mentioned previously in relation to the application envisaged.

The compound of the invention can be used in many fields of application, including the food and pharmaceutical sector, and in the perfumery industry.

A preferred field of application of the compound of the invention is for biscuits and cakes, and more particularly:

dry biscuits: sweet biscuits of the classical type, butter-biscuits, flavored biscuits, snack bars, shortbread, industrial cakes: champagne ladyfingers, thin finger biscuits, sponge biscuits, Genoa cake, sponge cake, madeleines, pound cake, fruit cakes, almond cakes, petit fours.

The main elements present in the mixtures intended for the aforementioned industries are proteins (gluten) and starch, which are most often supplied by wheat flour. For preparing the various types of biscuits and cakes, ingredients such as sucrose, salt, eggs, milk, fat, optionally chemical raising agents (sodium bicarbonate or other artificial raising agents) or biological raising agents and flours of various cereals etc., are added to the flour.

The compound of vanillin and ethylvanillin according to the invention is incorporated during manufacture, depending on the desired product, using the conventional techniques of the field in question (cf. notably J. L. KIGER and J. C. KIGER—Techniques Modernes de la Biscuiterie, Pâtisserie-Boulangerie industrielles et artisanales (Modern Techniques of Industrial and Traditional Production of Biscuits, Cakes and Bakery Products), DUNOD, Paris, 1968, Vol. 2, pp. 231 ff.).

Preferably, the compound of the invention is introduced in the fats that are used in the preparation of the dough.

As a guide, the compound of the invention is introduced in an amount from 0.005 to 0.2 g per kg of dough.

The compound of vanillin and ethylvanillin of the invention is perfectly suitable for use in chocolate making, regardless of the form in which it is used: bars of chocolate, couverture chocolate, chocolate filling.

It can be introduced during conching, i.e. mixing of cocoa paste with the various ingredients, notably flavoring agents, or after conching, by application in the cocoa butter.

In this field of application, the compound of vanillin and ethylvanillin of the invention is used, depending on the type of chocolate, at a rate from 0.0005 g to 0.1 g per 1 kg of finished product: the highest contents being used in couverture chocolate.

Another use of the compound of the invention is the manufacture of candies all kinds: sugared almonds, caramels, nougats, hard candy, fondant candies and others.

The amount of the compound of the invention introduced depends on the more or less strong taste that is desired. Thus, the doses of use of the compound of the invention can vary between 0.001% and 0.2%.

The compound of the invention is very suitable for uses in the dairy products industry and more particularly in flavored and gelified milks, entremets, yoghurts, ices and ice creams.

Flavoring is effected by simple addition of the compound of the invention, in one of the mixing stages required during manufacture of the product.

The contents of said compound to be used are generally low, of the order of 0.02 g per 1 kg of finished product.

Another application of the compound of the invention in the food industry is the preparation of vanillin sugar, i.e. impregnation of sugar with vanillin, in a content of the order of 7 g expressed relative to 1 kg of finished product.

The compound of the invention can also be included in various drinks and we may mention, among others, grenadine and chocolate drinks.

In particular, it can be used in preparations for instant drinks delivered by automatic drinks dispensers, flavored drinks in powder form, chocolate in powder form or else in instant preparations in the form of powder intended for making desserts of all kinds, custard tarts, pastes for cakes, pancakes, after diluting with water or with milk.

It is customary to use vanillin for denaturing butter. For this purpose, the compound of vanillin and ethylvanillin of the invention can be used at a rate of 6 g per tonne of butter.

Another field of application of the compound of the invention is animal feed, notably for the preparation of meal for feeding calves and pigs. The recommended content is about 0.2 g per kg of meal to be flavored.

The compound of the invention can find other applications such as a masking agent, for the pharmaceutical industry (for masking the odor of a medicinal product) or for other industrial products (such as gum, plastic, rubber etc.).

It is entirely suitable in quite different areas of industry such as cosmetics, perfumes or detergents.

It can be used in cosmetics such as creams, milks, make-up and other products and, as perfuming ingredients, in perfuming compositions, perfumed substances and products.

"Perfuming compositions" means mixtures of various ingredients such as solvents, solid or liquid carriers, fixing agents, various odor compounds, etc., in which the compound of the invention is incorporated, and is used for imparting the desired fragrance to various types of finished products.

Perfume bases constitute preferred examples of perfuming compositions in which the compound of the invention can be used advantageously at a content from 0.1 to 2.5 wt. %.

Perfume bases can be used for preparing numerous perfumed products, for example toilet waters, perfumes, after-shave lotions; toiletries and hygiene products such as bath or shower gels, deodorants or antiperspirants, whether in the form of sticks or lotions, talcs or powders of all kinds; products for the hair such as shampoos and hair products of all kinds.

Another example of application of the compound of the invention is soap-making. It can be used at a content from 0.3% to 0.75% of the total mass to be perfumed. Generally, in this application it is combined with benzoin resinoid and sodium hyposulfite (2%).

The compound of vanillin and ethylvanillin according to the invention can find many other applications, notably in room air deodorants or all maintenance products.

In the various applications mentioned above for purposes of illustration, the compound of the invention can be introduced alone or in the form of a composition containing it, together with one or more excipients, some examples of which were given above.

Examples illustrating the present invention, without limiting it, are given below.

In the examples, the percentages mentioned are expressed by weight.

EXAMPLE 1

Preparation of the Compound of the Invention 5.2 g of vanillin (VA) in powder form and 2.8 g of ethylvanillin (EVA) in powder form, i.e. a weight ratio VA/EVA=65/35, are put in a 125-ml bottle.

The mixture is homogenized by inverting the bottle several times.

The bottle is then placed in a stove at 70° C. for 2 hours in order to obtain complete melting.

The molten mixture is then poured into an aluminum dish preheated in the stove to 70° C.; the liquid is spread out so as to form a film of uniform thickness not exceeding 1 mm.

The dish is kept in the stove, the temperature of which is lowered from 70 to 51° C. at a rate of 1° C./min, followed by a plateau at 51° C. for at least an hour for complete solidification of the VA-EVA mixture.

The temperature of the stove is then lowered gradually to room temperature (about 1° C./min).

The solid bar obtained is ground moderately by means of an oscillating-arm granulator (Erweka FGS granulator) equipped with a sieve with mesh of 1.6 mm.

The compound of the invention obtained is in the form of granules.

Physicochemical Characteristics of the Compound of the Invention

1. The melting point of the compound of the invention is measured by differential scanning calorimetry.

Measurement is carried out with a Mettler DSC822e differential scanning calorimeter in the following conditions:
  sample preparation at room temperature: weighing and introduction in a sample holder,
  sample holder: crimped aluminum capsule,
  test sample: 8.4 mg,
  rate of temperature rise: 2° C./min,
  range investigated: 10-90° C.

The sample of the compound is weighed and is introduced into the capsule, which is crimped and then placed in the apparatus.

The temperature program is started and the fusion profile is obtained on a thermogram.

The melting point is determined from a thermogram obtained in the above operating conditions.

The onset temperature: temperature corresponding to the maximum slope of the fusion peak, is found.

The compound of the invention has a melting point, determined as previously described (T onset)=60° C.

2. The X-ray diffraction spectrum of the compound of the invention is determined by means of the X'Pert Pro MPD PANalytical instrument equipped with an X'Celerator detector, in the following conditions:
  Start Position [° 2Th.]: 1.5124
  End Position [° 2Th.]: 49.9794
  Step Size [° 2Th.]: 0.0170
  Scan Step Time [s]: 41.0051
  Anode Material: Cu
  K-Alpha1 [Å]: 1.54060
  Generator Settings: 30 mA, 40 kV It is compared with that of vanillin and of ethylvanillin.

Figure 1:
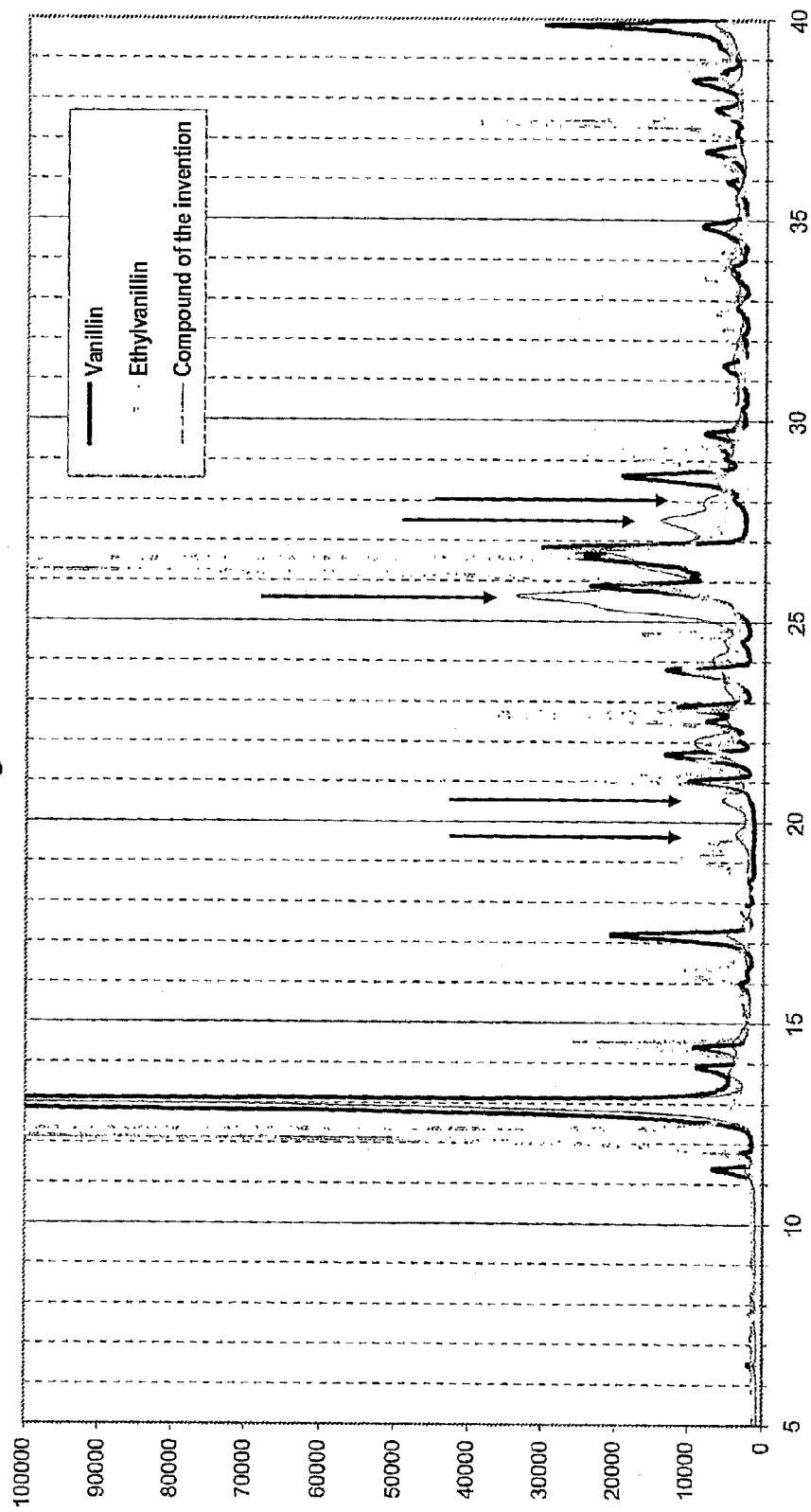
FIG. 1 shows the X-ray diffraction spectra of the compound of the invention, of vanillin, and of ethylvanillin.

FIG. 1 shows three curves corresponding to the different X-ray diffraction spectra of the compound of the invention, of vanillin and of ethylvanillin.

The X-ray diffraction spectrum of the compound of the invention shows several characteristic lines at angles 2θ (in °)=20.7-25.6-27.5-28.0 (measured relative to the line from copper K-Alpha1=1.54060 Å), which differentiates it from the spectra of vanillin and ethylvanillin.

The compound of the invention does not change after prolonged storage for 2 to 5 months at room temperature.

Figure 2:
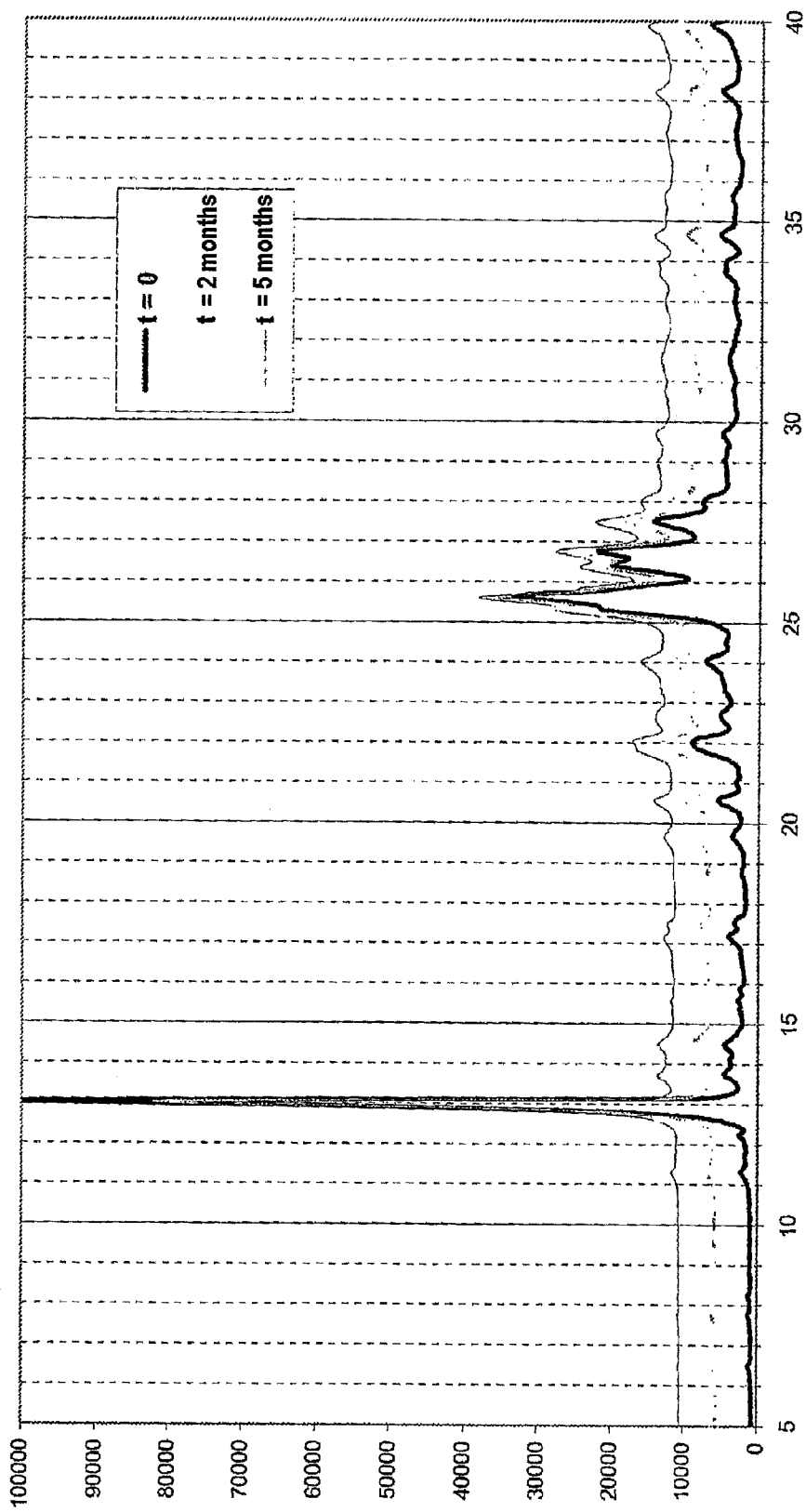
FIG. 2 shows the X-ray diffraction spectrum of the compound of the invention, as a function of the storage time.

Thus, FIG. 2 shows the variation of the X-ray diffraction spectrum of the compound of the invention, as a function of the storage time. It shows three curves corresponding to different X-ray diffraction spectra of the compound of the invention obtained at time t=0, then after storage for 2 months and 5 months.

The 3 curves obtained are normally superimposed. For better discrimination, two of the 3 curves in FIG. 2 have a baseline that is deliberately displaced relative to the reference baseline, which is the X-ray diffraction spectrum at time t=0. The curve corresponding to the X-ray diffraction spectrum obtained after storage for 2 months is displaced by 5000 pulses/s and that obtained after storage for 5 months is displaced by 10 000 pulses/s.

FIG. 2 demonstrates that the compound of the invention is unchanged after prolonged storage.

Figure 3:
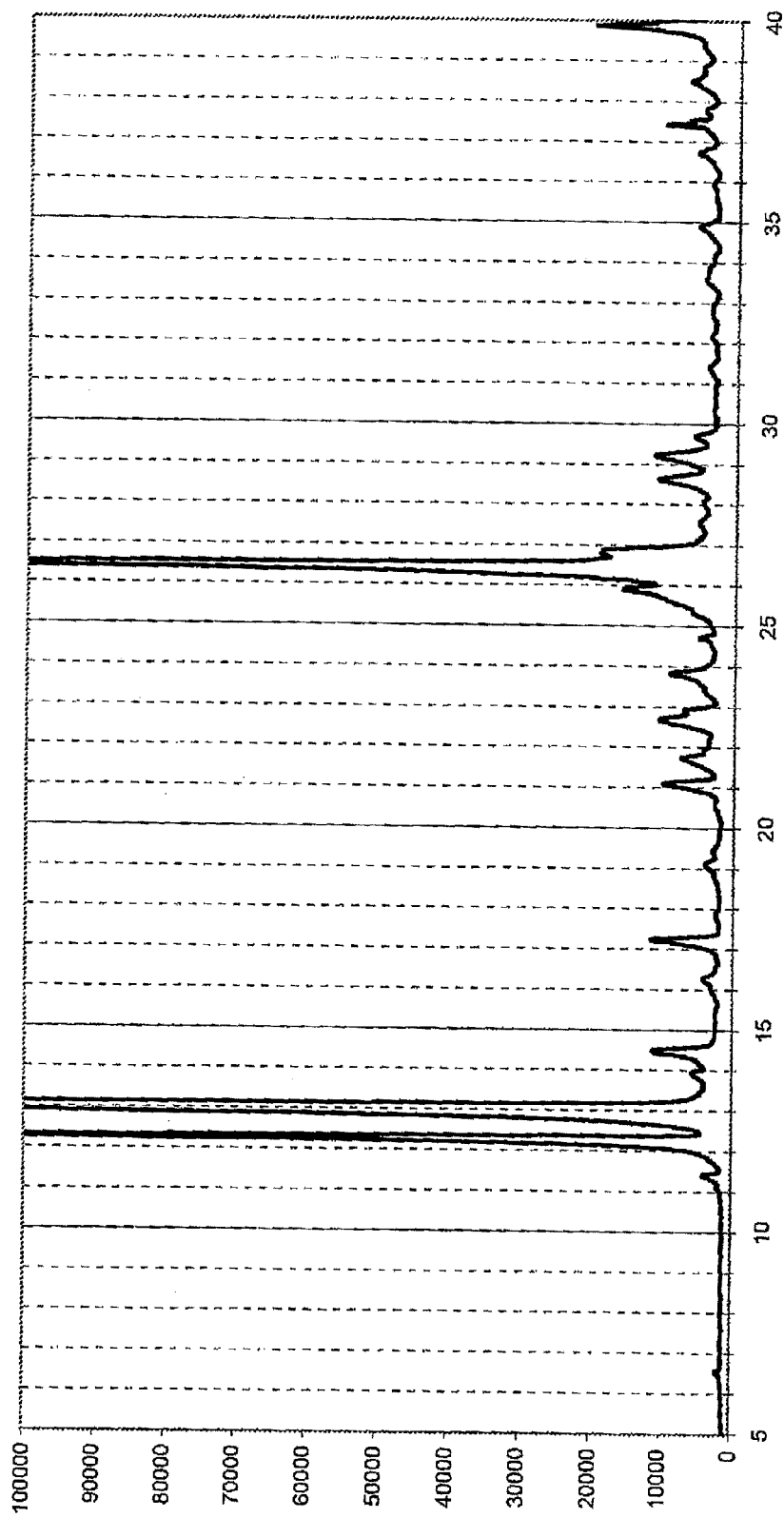
FIG. 3 shows the X-ray diffraction spectrum of a dry mixture of the two powders of vanillin and ethylvanillin in a molar ratio of 2.

FIG. 3 shows, for comparison, the X-ray diffraction spectrum of a dry mixture of the 2 powders of vanillin and ethylvanillin in a molar ratio of 2.

The conditions of measurement are as stated above.

The X-ray diffraction spectrum of the mixture does not have the characteristic lines of the compound of the invention.

3. As for the hygroscopicity, it is quantified from the weight gain of a sample of the compound of the invention placed in a thin layer (1 to 2 mm thick) in a climatic chamber at 40° C. in air at 80% relative humidity for 1 hour.

After holding for 1 hour at 40° C. in air at 80% relative humidity, the compound of the invention only adsorbs 0.270 of water by weight; this weight increase is fully reversible by returning to 25° C. at 40% relative humidity.

The granules obtained, stored for one month at 22° C. in a stoppered bottle, still display good flowability.

For comparison, a mixture of the 2 powders of vanillin and ethylvanillin, stored in the same conditions, has caked completely after a week regardless of the weight ratio VA/EVA between 2/98 and 98/2.

EXAMPLE 2

4.9 g of absolute ethanol, 5.2 g of vanillin and 2.8 g of ethylvanillin, i.e. a weight ratio VA/EVA=65/35, are put in a 125-ml bottle.

The bottle is stirred by means of a bottle roller and is maintained at 25° C. until the 2 products have dissolved completely (about 2 hours).

The bottle is then placed in a refrigerator at 3° C. for about ten hours.

There is appearance of a white solid phase, which is quickly separated from the liquid by filtration.

The solid thus obtained is dried under vacuum (100 mm of mercury), firstly at 20° C. for one hour, then slowly increasing the temperature at a rate of 1° C./min to 52° C.

Drying under vacuum (100 mm of mercury) is continued at 52° C. for one hour.

The dry product has a melting point of 61° C. measured by differential scanning calorimetry.

Its X-ray diffraction spectrum has the characteristic lines that differentiate it from vanillin and ethylvanillin.

EXAMPLE 3

8.5 g of vanillin, 4.6 g of ethylvanillin and 1.0 g of demineralized water are put in a 125-ml bottle.

This bottle is placed in a stove at 62° C. for 2 hours so as to obtain a single homogeneous liquid phase.

This liquid is poured into an aluminum dish and is spread out so as to form a film of uniform thickness.

The dish is then placed in a refrigerator at 3° C. for about ten hours.

Complete caking of all of the product is observed.

After it returns to room temperature, the product is still solid, and is ground moderately by means of an oscillating-arm granulator (Erweka type FGS granulator) equipped with a sieve with mesh of 1.6 mm.

The compound of the invention obtained in the form of granules is dried under vacuum (100 mm of mercury), first at 20° C. for one hour and then slowly increasing the temperature at a rate of 1° C./min to 52° C.

Drying under vacuum (100 mm of mercury) is continued at 52° C. for one hour.

The dry product has a melting point of 60° C. measured by differential scanning calorimetry.

Its X-ray diffraction spectrum has the characteristic lines that differentiate it from vanillin and ethylvanillin.

EXAMPLES 4 TO 6

Granules of the compound of the invention (example 4) and compositions containing them (examples 5 and 6) are prepared in examples 4 to 6.

Their storage behavior is observed in comparison with vanillin (comparative example A), ethylvanillin (comparative example B) and a dry mixture of vanillin and ethylvanillin (comparative example C).

EXAMPLE 4

350 g of vanillin in powder form and 188.5 g of ethylvanillin in powder form, i.e. a molar ratio of vanillin to ethylvanillin of 2, are put in a stirred reactor equipped with double-jacket heating. The moisture content of these powders is 0.1±0.02 wt. %.

This mixture is heated to 70° C. with stirring. A homogeneous liquid phase is thus obtained.

The molten mixture is poured onto a stainless steel plate maintained at 50° C. so as to form a thin film on it with thickness of about 1 mm. Crystallization is complete in about ten minutes.

The solid sheet thus formed detaches easily from the stainless steel; it is left at room temperature until it has cooled completely.

This sheet is then crushed coarsely for feeding into an oscillating-arm granulator (Erweka type FGS granulator) equipped with a sieve with mesh of 1.0 mm. There, the product is ground moderately to give granules with size varying from 0.1 to 1.0 mm.

Figure 4:
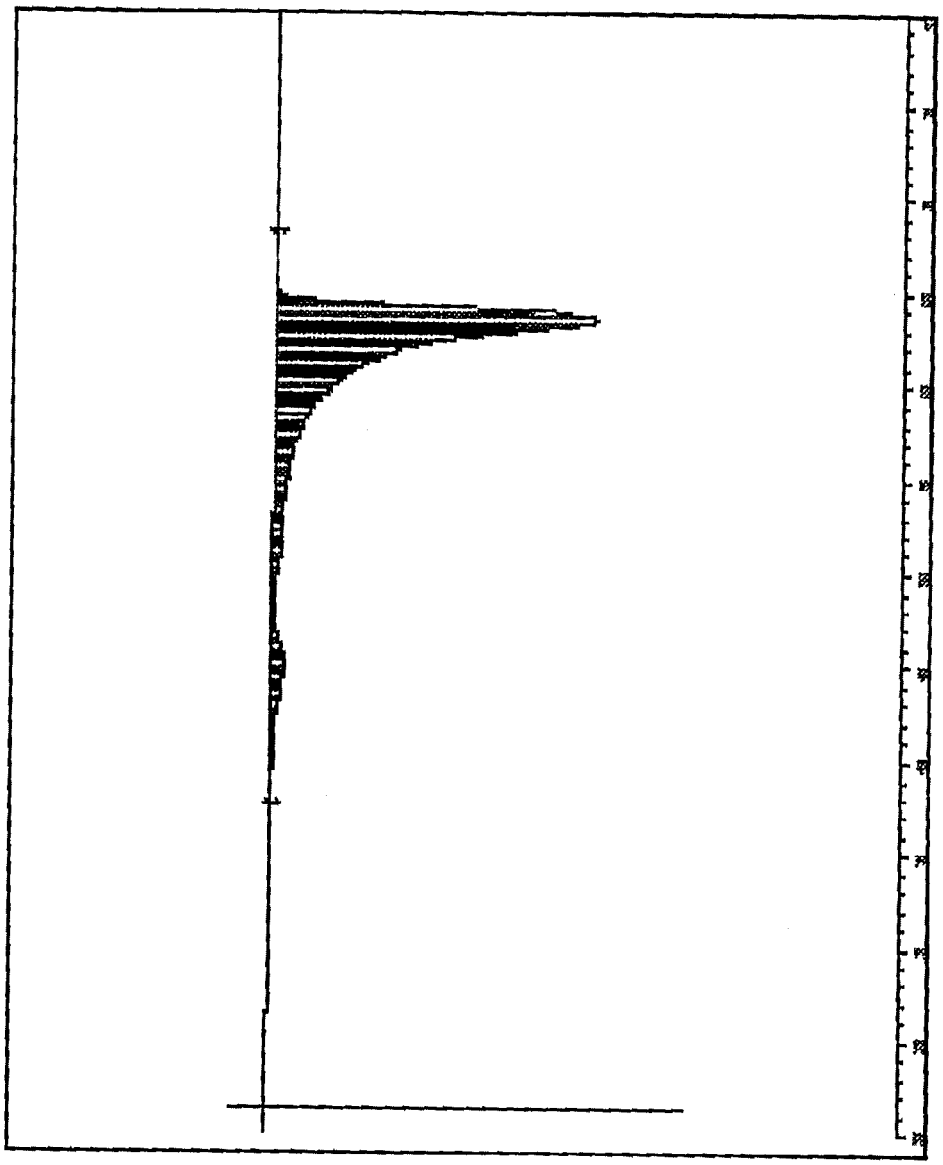
FIG. 4 shows the thermogram of the granules of Example 4.

The granules thus obtained have a melting point of 59.8° C. measured by differential scanning calorimetry (T onset) and determined from the thermogram shown in FIG. 4.

The thermogram is a graph showing the thermal power supplied to the sample (expressed in w/g) as a function of temperature between 20° C. and 90° C.

The enthalpy of fusion, 129.5 J/g, can be found from the integral of the curve obtained.

Their X-ray diffraction spectrum has characteristic lines at angles 2θ (°)=20.7-25.6-27.5-28.0, which differentiate it from the spectra of vanillin and ethylvanillin, as shown in FIG. 1.

EXAMPLE 5

The granules prepared according to example 4 can be mixed dry with an excipient, for example at 50/50 by weight, which further improves their flowability.

In this example, a composition is prepared comprising 50 wt. % of the granules prepared according to example 4 and 50 wt. % of an excipient, sucrose.

The mixing operation of about 5 min is carried out at room temperature in a WAM plough mixer.

EXAMPLE 6

In this example, a composition is prepared comprising 50 wt. % of the granules prepared according to example 4 and 50 wt. % of a maltodextrin having a DE of 6 (Roquette Glucidex IT6).

The mixing operation is carried out as described in example 5.

COMPARATIVE EXAMPLES A TO C

These examples relate respectively to vanillin, ethylvanillin and the dry mixture of powders of vanillin and ethylvanillin in a molar ratio of 2, produced in a mixer as in example 4.

The flowability and susceptibility to lumping of the compound of the invention and of the compositions employing it are compared with that of vanillin powder, ethylvanillin powder and a simple dry mixture of these 2 powders.

The flowability of powders is a technical concept that is familiar to a person skilled in the art. For more detail, reference may be made notably to the work "Standard shear testing technique for particulate solids using the Jenike shear cell", published by The Institution of Chemicals Engineers, 1989 (ISBN: 0 85295 232 5).

The flowability index is measured in the following way.

The flowability of powders is measured by shearing a sample in an annular cell (marketed by D. Schulze, Germany).

Preshearing of the powders is carried out under a normal stress of 5200 Pa.

The shearing points required for plotting the flow locus of the sample are obtained for 4 normal stresses below the preshearing stress, typically 480 Pa, 850 Pa, 2050 Pa and 3020 Pa.

From the Mohr circles in the diagram "shear stress as a function of normal stresses", 2 stresses that characterize the sample are determined on the flow locus:
 the normal stress in the principal direction; it is given by the extremity of the large Mohr circle passing through the preshearing point,
 the force of cohesion; it is given by the extremity of the small Mohr circle that is tangential to the flow locus and passes through the origin.

The ratio of the normal stress in the principal direction to the force of cohesion is a dimensionless number called "i, flowability index".

These measurements are performed immediately after filling the annular cell, and we thus obtain the instantaneous flowability index.

Another series of measurements is performed with a cell that had been stored for 24 hours at 40° C. and 80% relative humidity at a normal stress of 2400 Pa.

This gives the lumpiness index.

The results presented in Table (I) make it possible to compare the instantaneous flowability indices and lumpiness indices of vanillin powder (comparative example A), ethylvanillin powder (comparative example B), a simple dry mixture of these 2 powders (comparative example C), granules obtained according to the method of the invention (example 4), granules obtained according to the method of the invention and mixed 50/50 by weight with sucrose (example 5), granules obtained according to the method of the invention and mixed 50/50 by weight with a maltodextrin (example 6).

TABLE I

| Reference | Nature of the product | Instantaneous flowability index | Lumpiness index after storage |
|---|---|---|---|
| Comparative example A | Vanillin powder | 5.6 | 0.66 |

TABLE I-continued

| Reference | Nature of the product | Instantaneous flowability index | Lumpiness index after storage |
|---|---|---|---|
| Comparative example B | Ethylvanillin powder | 6.5 | 0.61 |
| Comparative example C | Mixture of powdered vanillin and ethylvanillin molar ratio = 2 | 18 | 0.03 |
| Example 4 | Granules of the invention described in example 4 | 22 | 0.13 |
| Example 5 | Composition comprising granules from example 4 and sucrose | 20 | 0.18 |
| Example 6 | Composition comprising granules from example 4 and a maltodextrin | 34 | 0.73 |

It is found that the granules obtained according to the method of the invention have a lumpiness index after storage under stress far higher than that of a simple dry mixture of powders of vanillin and ethylvanillin.

When mixed 50/50 by weight with a maltodextrin, these granules have a lumpiness index comparable to that of powders of pure vanillin or of pure ethylvanillin.

The invention claimed is:

1. A crystalline form of 2:1 vanillin/ethylvanillin, characterized by:
   a melting point of 60° C.±2° C.; and
   an X-ray diffraction spectrum with several characteristic lines at angles 2θ (in°)=20.7-25.6-27.5-28.0 (measured relative to the line of copper K-Alpha1=1.54060 Å); said lines not being present in the X-ray diffraction spectrum of pure vanillin and of pure ethylvanillin.

2. The crystalline form as claimed in claim 1, wherein the crystalline form adsorbs less than 0.5 wt. % of water and remains solid at 40° C. in air at 80% relative humidity.

3. The crystalline form as claimed in claim 1, wherein the crystalline form displays improved flowability and absence of lumpiness after storage at 22° C. for 1 month.

4. A method of preparing the crystalline form as claimed in claim 1, wherein the method comprises cocrystallizing vanillin and ethylvanillin in a vanillin/ethylvanillin molar ratio of 2, in a molten medium or in solution in a solvent that dissolves them.

5. The method as claimed in claim 4, wherein when the vanillin and ethylvanillin are in the solvent, they are dissolved in the solvent with heating and stirring, and then cooled to obtain crystals, which are then separated.

6. The method as claimed in claim 5, wherein the solvent is water and/or a protic or aprotic polar organic solvent.

7. The method as claimed in claim 5, wherein the solvent is selected from the group consisting of:
   water;
   an alcohol;
   an ether-oxide; and
   an alkyl ester or an aralkyl ester of an aliphatic, cycloaliphatic, or aromatic carboxylic acid.

8. The method as claimed in claim 5, wherein the solvent is selected from the group consisting of water, ethanol, propylene glycol, triacetin and mixtures thereof.

9. The method as claimed in claim 5, wherein the amount of solvent used, expressed by weight relative to the weight of dry matter (vanillin+ethylvanillin), is from 5% to 60%.

10. The method as claimed in claim 4, wherein the vanillin and ethylvanillin are melted to produce a molten mixture that is cooled at a temperature of 50° C.±1, which is maintained until the molten mixture has solidified.

11. The method as claimed in claim 10, wherein the vanillin and ethylvanillin are charged, separately or mixed together, and heated to a temperature that is selected in the range from 60° C. to 90° C.

12. The method as claimed in claim 11, wherein the molten mixture is prepared under an atmosphere of inert gas.

13. The method as claimed in claim 10, wherein the molten mixture is cooled without stirring.

14. The method as claimed in claim 4, wherein the crystalline form obtained is formed by a grinding technique.

15. The method as claimed in claim 10, wherein the molten mixture is formed by a flake-forming technique.

16. The crystalline form as claimed in claim 1, wherein the crystalline form is obtained by melting a mixture of vanillin and ethylvanillin having a vanillin/ethylvanillin molar ratio of 2 at a temperature selected in the range from 60° C. to 90° C., followed by cooling of the molten mixture to a temperature of 50° C.±1, maintaining the temperature until the mixture has solidified, and grinding the mixture to obtain the crystalline form in powder form.

17. A composition comprising the crystalline form as claimed in claim 1 and further comprising at least one excipient.

18. The composition as claimed in claim 17, wherein the excipient is selected from the group consisting of:
   a sugar;
   a starch;
   a starch hydrolyzate;
   a dextrin or a maltodextrin;
   a cellulose;
   a gum;
   a flour;
   a gelatin;
   a silica;
   an antioxidant;
   an emulsifier;
   a vanillin; and
   an ethylvanillin.

19. The composition as claimed in claim 17, comprising from 0.1 wt. % to 90 wt. % of said at least one excipient based on the total weight of said composition.

20. A composition comprising the crystalline form as claimed in claim 1, wherein the composition is a flavoring agent for human or animal nutrition, a pharmaceutical composition, a perfume, a cosmetic composition, or a detergent.

21. The composition as claimed in claim 20, wherein the composition is used to manufacture dough; chocolate; candy; a dairy product; a vanillin sugar; a drink; or an instant drink; or for denaturing butter.

22. The composition as claimed in claim 20, wherein the composition is used in animal feed.

23. The composition as claimed in claim 20, wherein the composition is used as an odor masking agent; in the preparation of creams, milks and make-up for cosmetics; as a perfuming base; or as a detergent.

24. The crystalline form as claimed in claim 2, wherein the crystalline form adsorbs between 0.1 wt. % and 0.3 wt. % of water.

25. The method as claimed in claim 7, wherein the solvent is an alcohol that is an aliphatic alcohol or an arylaliphatic alcohol.

26. The method as claimed in claim 7, wherein the solvent is an alcohol selected from the group consisting of methanol, ethanol, propanol, isopropanol, butanol, β-phenylethyl alcohol, ethylene glycol, diethylene glycol, propylene glycol and glycerol.

27. The method as claimed in claim 7, wherein the solvent is an ether selected from the group consisting of diethyl ether, dipropyl ether, diisopropyl ether, dibutyl ether, methyl tert-butyl ether, ethyl tert-butyl ether, ditert-butyl ether, ethylene glycol dimethyl ether, and diethylene glycol dimethyl ether.

28. The method as claimed in claim 7, wherein the solvent is an alkyl or an aralkyl of an aliphatic, cycloaliphatic or aromatic carboxylic acid selected from the group consisting of ethyl acetate, butyl acetate, benzyl salicylate, methyl laurate, methyl benzoate, ethyl citrate, triacetylglycerol or triacetin, ester of glycerol, and ester of acetic acid.

29. The method as claimed in claim 11, wherein the vanillin and ethylvanillin are heated to a temperature between 70° C. and 80° C.

30. The method as claimed in claim 12, wherein the inert gas is nitrogen.

31. The crystalline form as claimed in claim 16, wherein the mixture of vanillin and ethylvanillin is melted at a temperature between 70° C. and 80° C.

32. The composition as claimed in claim 18, wherein the excipient is a sugar selected from the group consisting of glucose, sucrose, fructose, galactose, ribose, maltose, sorbitol, mannitol, xylitol, lactitol, maltitol, an invert sugar, glucose syrup, a sucroglyceride derived from fatty oil, copra oil, palm oil, hydrogenated palm oil, hydrogenated soya oil; a sucroester of a fatty acid, sucrose monopalmitate, sucrose monodistearate, and sucrose distearate.

33. The composition as claimed in claim 18, wherein the excipient is a starch selected from the group consisting of a starch derived from wheat, a starch derived from maize, a starch derived from barley, a starch derived from rice, a starch derived from manioc, a starch derived from potato, a native starch, a pregelatinized starch, a modified starch, an amylose-rich native maize starch, a pregelatinized maize starch, a modified maize starch, a modified waxy maize starch, a pregelatinized waxy maize starch, a modified waxy maize starch, and a OSSA/sodium octenylsuccinate starch.

34. The composition as claimed in claim 18, wherein the excipient is a cellulose selected from the group consisting of a cellulose ether, a cellulose ester, a methylcellulose, an ethylcellulose, a methylethylcellulose, a hydroxypropylcellulose, a carboxymethylcellulose, and a carboxyethylcellulose optionally in a sodium form.

35. The composition as claimed in claim 18, wherein the excipient is a gum selected from the group consisting of kappa carrageenan, iota carrageenan, pectin, guar gum, carob gum, xanthan gum, an alginate, gum arabic, acacia gum, and agar-agar.

36. The composition as claimed in claim 18, wherein the excipient is a flour selected from the group consisting of a wheat flour, a native wheat flour, a pregel wheat flour, a starch, and a potato starch.

37. The composition as claimed in claim 18, wherein the antioxidant is vitamin E.

38. The composition as claimed in claim 18, wherein the emulsifier is lecithin.

39. The composition as claimed in claim 17, wherein the at least one excipient is selected from the group consisting of a fat; a fatty alcohol; a sugar polysaccharide; a silica; a vanillin; and an ethylvanillin.

40. The crystalline form as claimed in claim 1, consisting of less than 0.5 wt. % of adsorbed water.

41. The crystalline form as claimed in claim 1, consisting of between 0.1 wt. % and 0.3 wt. % of adsorbed water.

* * * * *